US005674715A

United States Patent [19]
Tomita et al.

[11] Patent Number: 5,674,715
[45] Date of Patent: Oct. 7, 1997

[54] METHOD FOR PRODUCING URIDINE DIPHOSPHATE N-ACETYLGLUOSAMINE

[75] Inventors: Minoru Tomita; Hisao Mukai, both of Naruto, Japan

[73] Assignee: Tomita Pharmaceutical Co., Ltd., Tokushima-ken, Japan

[21] Appl. No.: 435,152

[22] Filed: May 5, 1995

[30] Foreign Application Priority Data

May 12, 1994 [JP] Japan .................................. 6-098961
Jun. 1, 1994 [JP] Japan .................................. 6-120364

[51] Int. Cl.⁶ .......................... C12P 19/30; C12P 19/02; C12P 19/12; C12P 19/28
[52] U.S. Cl. .......................... 435/89; 435/100; 435/105; 435/85; 435/72
[58] Field of Search .......................... 435/89, 100, 105, 435/85, 72

[56] References Cited

PUBLICATIONS

Tomita; J.Brew.Soc. Japan vol. 83, No. 11, pp. 770–774 (1988); "Intracellular Nucleotides and Amino Acids of Zygosaccharomyces rouxii, in relation to the Salt–tolerant Regulation".

Strominger, et al.; J.Biol.Chem., vol. 234, No. 7, pp. 1828–1829 (1959); "The Preparation of Uridine Diphospho-acetylgalactosamin:".

Tochikura, et al.; Agr.Biol.Chem., vol. 35, No. 2, pp.163–176 (1971); "Studies on Microbial Metabolism of Sugar Nucleotides Part VI".

Tomita; J.Ferment.Technol., vol.61, No. 2, pp. 205–209 (1983); "Isolation and Identification of UDP–N–Acetylglu-cosamine from Cells of Saccharomyces rouxii".

Cabib, et al.; "Uridine Diphosphate Acetylglucosamine" (1953); pp. 1055–1070.

Primary Examiner—Michael G. Wityshyn
Assistant Examiner—Francisco C. Prats
Attorney, Agent, or Firm—Knobbe, Martens, Olson & Bear, LLP

[57] ABSTRACT

A method for producing uridine diphosphate N-acetylglucosamine comprising culturing osmo-tolerant yeasts in aerobic conditions in a medium having inorganic salt concentration of about 2–8%.

5 Claims, 1 Drawing Sheet

METHOD FOR PRODUCING URIDINE DIPHOSPHATE N-ACETYLGLUOSAMINE

FIELD OF THE INVENTION

The present invention relates to a method for producing high-purity and low-cost uridine diphosphate N-acetylglucosamine (UDP-N-acetylglucosamine) in a large scale.

In the specification, "%" means "% (W/V)".

BACKGROUND OF THE INVENTION

Recently, because of increasing expectation of biologically active sugar chains as a drug, research on synthesis of sugar chains is sharply competed worldwide. Some sugar chains as a reagent are conventionally available at present on the market. However, the sugar chains are very expensive and limited in kind and quantity. Sugar chains are produced according to a method of extraction from natural products, chemical synthesis, enzymatic synthesis or a mixture thereof. A method of enzymatic synthesis is regarded as the most suitable method, because the method employing enzyme is more advantageous to synthesize sugar chains having a very specific structure effectively than any other methods.

Sugar transferases and sugar nucleotides as a substrate of the transferases are necessary to synthesize sugar chains by an enzymatic method. A large-scale synthesis of sugar transferases is becoming possible with the progress of biotechnology. Manufacturing cost of sugar nucleotides as a substrate is gradually decreasing. In contrast, a method of large-scale production of UDP-N-acetylglucosamine, which is a key substance of many biologically active sugar chains as a doner of N-acetylglucosamine, has not been established due to technical and profitable problems.

The inventors inventigated physiological activities of osmo-tolerant yeasts to brew miso heretofore. We reported with respect to the investigation that *Zygosaccharomyces rouxii* accumulates UDP-N-acetylglucosamine when cultured in the presence of 1M NaCl (Journal of the Brewing Society, vol. 83, No. 11, pp. 770–774, 1988).

However, a great amount of low-cost UDP-N-acetylglucosamine can not be produced, because the amount of UDP-N-acetylglucosamine accumulated is small.

It is an object of the invention to provide a method of mass and low-cost synthesis of UDP-N-acetylglucosamine whose demand increases worldwide with the rapid progress of technology in the field of glycotechnology.

DISCLOSURE OF THE INVENTION

Figure 1:
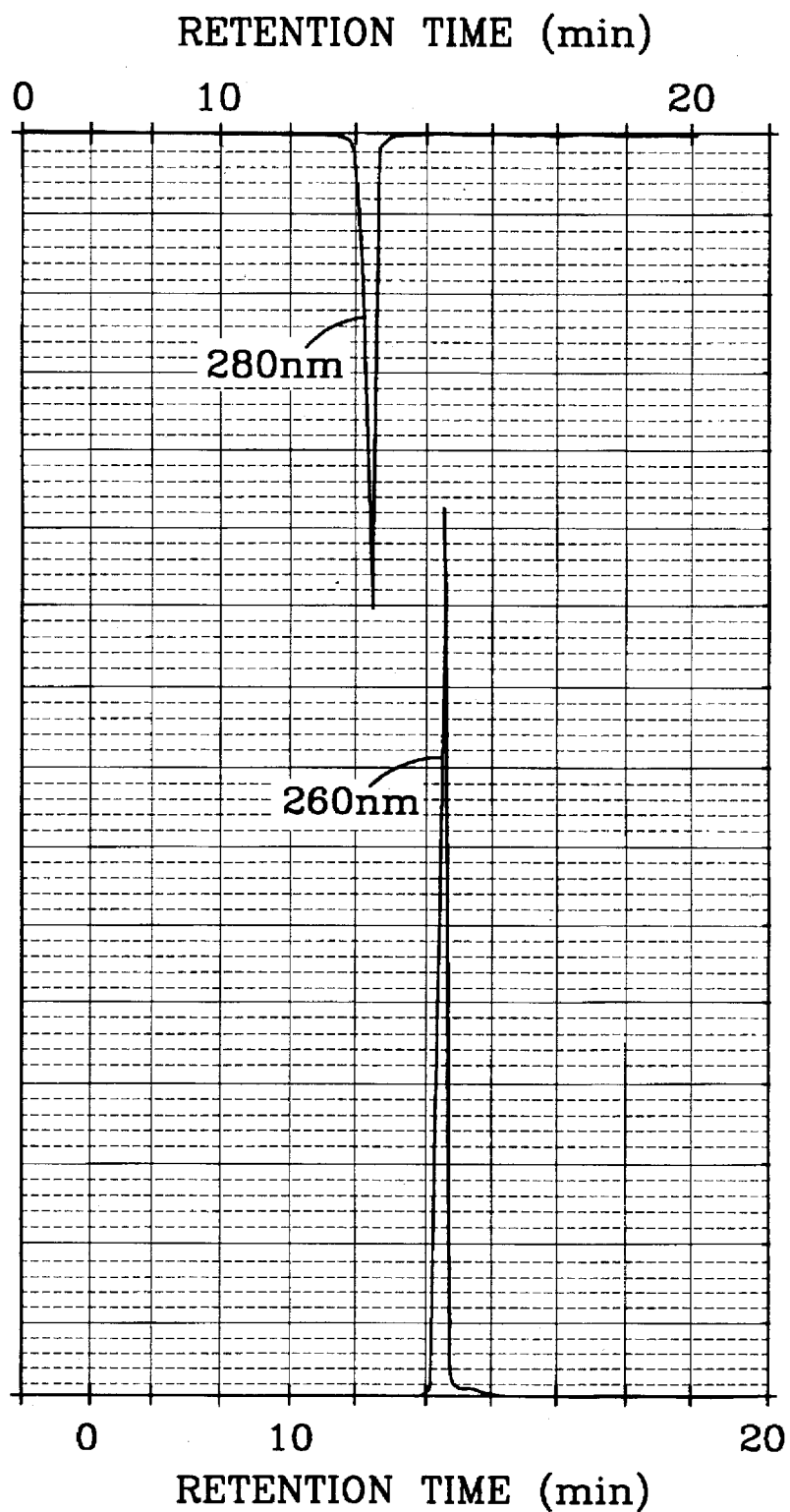
FIG. 1 is a chart showing results of HPLC analysis of UDP-N-acetylglucosamine obtained in example 1.

The inventors, noting that yeasts belonging to Zygosaccharomyces genus accumulate UDP-N-acetylglucosamine under high salt concentration as high as 1M, have conducted extensive research on elevating accumulation efficiency of UDP-N-acetylglucosamine by said yeasts and found that said yeasts accumulate UDP-N-acetylglucosamine under aerobic conditions in a large scale and accomplished the invention.

Thus, the present invention provides a method for producing uridine diphosphate N-acetylglucosamine comprising culturing osmo-tolerant yeasts in aerobic conditions in a medium having inorganic salt concentration of about 2–8%.

Examples of osmo-tolerant yeasts are yeasts belonging to Zygosaccharomyces genus, Pichia genus, Debaryomycos genus, Hansenula genus and Candida genus, preferably yeasts belonging to Zygosaccharomyces genus.

In the specification, "osmo-tolerant yeasts" means yeasts being capable of suitably growing in a medium having salt concentration of at least 2%, provided that said yeasts may be grown in a medium having salt concentration of 2% or less.

The osmo-tolerant yeasts including Zygosaccharomyces genus are researched in relation to production of miso and soy sause in Japan, but are regarded as destructive fungus causing pollution of honey, etc., in western countries. Therefore, the yeasts of the invention are hardly taken into consideration for substance production. The research on osmo-tolerant yeasts conducted by the inventors is carried out as a part of technology of microbial control for production of brewing miso.

In the specification, the osmo-tolerant yeasts belonging to Zygosaccharomyces genus are not specifically limited to, but include *Zygosaccharomyces rouxii* and *Zygosaccharomyces bailii*. In addition, yeasts belonging to Pichia genus include *Pichia farinosa*, yeasts belonging to Debaryomycos genus include *Debaryomycos hansenii*, and yeasts belonging to Candida genus include *Candida versatilis*.

The yeasts of the invention are cultured in a medium with inorganic salt concentration of about 2–8%. The inorganic salts include sodium chloride, potassium chloride, magnesium chloride, calcium chloride, sodium bromide and like alkali metal halides and alkaline earth metal halides; sodium phosphate, sodium dihydrogen phosphate, disodium hydrogen phosphate, potassium phosphate, potassium dihydrogen phosphate, dipotassium hydrogen phosphate, calcium phosphate, magnesium phosphate, and like alkali metal phosphates and alkaline earth metal phosphates; sodium nitrate, potassium nitrate, magnesium nitrate, calcium nitrate and like alkali metal nitrates and alkaline earth metal nitrates; sodium sulfate, potassium sulfate, magnesium sulfate, calcium sulfate and like alkali metal sulfates and alkaline earth metal sulfates. The inorganic salts are employed singly or in a mixture thereof. Preferable inorganic salts are sodium chloride, potassium chloride, sodium sulfate, sodium nitrate, etc. The osmo-tolerant yeasts are preferably cultured in a medium in which total inorganic acid concentration ranges about 2–8%.

Natural medium and artificial medium suitably containing carbon source, nitrogen source, inorganic substances, etc., may be employed to culture said osmo-tolerant yeasts, as long as the medium containing said inorganic salts in said range of concentration has high osmotic pressure. The carbon source, nitrogen source and inorganic substances are not specifically limited to, but easily selected from known substances. A pH value of said medium ranges about 3–8, preferably about 4–6.

According to the method of the invention, said osmo-tolerant yeasts are cultured in an aerobic condition. Preferable aerobic condition is about 1–7 ppm in concentration of dissolved oxygen, preferably about 2–7 ppm. Although the concentration of dissolved oxygen is maintained throughout culture period, the concentration of dissolved oxygen may be below said concentration as long as said concentration of dissolved oxygen is maintained for a certain period of time. A culture period to maintain said concentration of dissolved oxygen is changed with culture conditions, but usually about 2-4 days. Culture is preferably conducted with agitation or shake. The most preferable method of the invention is aerobic agitation culture method. In the process of the invention, higher efficiency of oxygen supply makes it possible to elevate productivity of the substance, i.e., UDP-N-acetylglucosamine.

When said yeasts of the invention are cultured, oxygen is prosperously consumed with increase of yeasts. The rate of oxygen consumption reaches the peak after start of culture for 30–72 hours, although the peak time varies depending on salt concentration and the number of yeasts inoculated. A suitable temperature for culture is not specifically limited to, but usually about 25°–35° C., preferably about 30° C.

Production yield according to the invention is 20–40 mg per 1 g of dry yeast. The yield of the production method of the invention is good enough for application to production of UDP-N-acetylglucosamine in an industrial scale.

As mentioned above, the yeasts have been utilized in stationary fermentation under high salt concentration for production of miso and soy sause, and have hardly been utilized as yeasts for fermentation of industrial scale. The invention has first found that production of UDP-N-acetylglucosamine is increased by culturing osmo-tolerant yeasts in the presence of inorganic salts of high concentration under predetermined concentration of dissolved oxygen. The invention enables low-cost and large-scale production of UDP-N-acetylglucosamine leading to enabling synthesis of sugar chains having a variety of structures.

BEST MODE FOR CARRYING OUT THE INVENTION

The present invention will be described below in greater detail using examples and comparative examples. However, the invention is not limited to the examples.

EXAMPLE 1

Affection of salt concentration in medium on production of UDP-N-acetylglucosamine Zygosaccharomyces rouxii ATCC 52698 strain was aerobically cultured in 8 L volume of jar fermentor containing 5 L of liquid medium under conditions of 30° C., 72 hours, 2.5 L/min (aeration volume) and 300 rpm (agitation number). Each liquid medium was prepared by adding glucose (1%), peptone (0.5%), yeast extract (0.1%) and sodium chloride (0, 1, 2, 4, 6, 8, 10 and 12%). A 50 ml. of culture medium, prepared by shaking culture at 30° C. for 48 hours in said medium except that sodium chloride was not included, was added to the culture medium as spawn. After culture process, yeasts were collected by centrifuging 1 L of each culture medium. To the yeasts was added 300 ml of 5% perchloric acid pre-cooled sufficiently, and the resulting mixture was well mixed and allowed to stand for 1 hour. The yeast suspension was neutralized with 10% aqueous potassium hydroxide solution and filtrated to give clear extract. The extract was diluted with water to a correct volume of 1 L. A 10 μl of the diluted extract was analyzed by high performance liquid chromatography (HPLC) to determine UDP-N-acetylglucosamine. The weight of yeast was determined as dry weight. Specifically, yeasts collected by centrifugation of culture medium (1 L) were washed twice with distilled water, dried at 105° C. for 4 hours and then weighed.

As comparison, the same procedure as above was repeated except that Saccharomyces cereviceae, baker's yeast, was employed in place of Zygosaccharomyces rouxii ATCC 52698 strain at sodium chloride concentration of 0 and 4%.

<Result>

As shown in table 1, when concentration of sodium chloride in culture medium was 2% or more, production of UDP-N-acetylglucosamine per unit dry yeast was increased rapidly. However, increase of sodium chloride causes decrease of the amount of yeast obtained leading to decrease of yield of UDP-N-acetylglucosamine per unit culture medium. Therefore, sodium chloride concentration preferably ranges about 2–8% more preferably around 4%.

The baker's yeasts as comparison increase in a medium free of sodium chloride very rapidly, but hardly produce UDP-N-acetylglucosamine. The baker's yeasts increase in a small extent in a medium having 4% sodium chloride concentration. In both medium, yield of UDP-N-acetylglucosamine by baker's yeasts is very small.

TABLE 1

|  | NaCl Concentration (%) | Yield per Medium (mg/L) | Yield per Yeast (mg/g) | Yeast Weight (g/L) |
| --- | --- | --- | --- | --- |
| Example 1 | 0 | 4 | 0.6 | 7.2 |
|  | 1 | 12 | 1.8 | 6.6 |
|  | 2 | 136 | 23.1 | 5.9 |
|  | 4 | 220 | 40.0 | 5.5 |
|  | 6 | 182 | 39.6 | 4.6 |
|  | 8 | 125 | 39.1 | 3.2 |
|  | 10 | 63 | 30.0 | 2.1 |
|  | 12 | 45 | 28.1 | 1.6 |
| Comparison | 0* | 1 | 0.1 | 10.5 |
|  | 4* | — | 0.2 | 1.2 |

*) demonstrates production yield of conventional baker's yeast.

EXAMPLE 2

Affection of aeration agitation conditions in medium on production of UDP-N-acetylglucosamine <Method>

The same culture process as example 1 was repeated at sodium chloride concentration of 4% except that aeration volume and agitation number in jar fermentor varied as shown in table 2. In table 2, "1 vvm" means that aeration volume per 1 minute is the same as the volume of culture medium (i.e., 5 L/min in this example). Concentration of dissolved oxygen was determined with DO meter continuously throughout the cultivation period.

<Result>

As shown in table 2, production of UDP-N-acetylglucosamine is improved under more aerobic conditions. UDP-N-acetylglucosamine may be produced in a medium in which minimum dissolved oxygen concentration is less than 1 ppm. However, aeration agitation conditions maintaining the concentration of at least 1 ppm all the time are more preferable to produce UDP-N-acetylglucosamine more sufficiently.

TABLE 2

|  | Plot (Number) | Aeration Volume (vvm) | Agitation Number (rpm) | Minimum DO (ppm)* | Yield (mg/L) |
| --- | --- | --- | --- | --- | --- |
| Example 2 | 1 | 0 | 0 | 0 | 20 |
|  | 2 | 0.5 | 0 | 0.1 | 45 |
|  | 3 | 0 | 300 | 0.2 | 52 |
|  | 4 | 0.1 | 300 | 0.4 | 110 |
|  | 5 | 0.2 | 300 | 1.0 | 215 |

TABLE 2-continued

| Plot (Number) | Aeration Volume (vvm) | Agitation Number (rpm) | Minimum DO (ppm)* | Yield (mg/L) |
|---|---|---|---|---|
| 6 | 0.5 | 300 | 1.5 | 220 |
| 7 | 1.0 | 300 | 1.8 | 224 |

*) minimum concentration of dissolved oxygen
**) production of UDP-N-acetylglucosamine per culture medium (1L)

EXAMPLE 3

Large scale production of UDP-N-acetylglucosamine sodium salt employing sodium chloride-containing medium A medium containing glucose (1%), peptone (0.5%), yeast extract (0.2%), potasium dihydrogen phosphate (0.1%), magnesium sulfate (0.05%) and sodium chloride (4%) was employed as seed medium.

A 10 liter of pre-culture medium prepared by aerobically culturing seed medium in which Zygosaccharomyces rouxii ATCC 52698 strain was inoculated was added to 1 kL of the culture medium in 2-ton type aerobic agitation culture tank and cultured at 30° C., for 72 hours under aerobic agitation conditions of 500 L/min (aeration volume) and 200 rpm (agitation number). After culture step, yeasts were separated by centrifugation to give 20.2 kg of yeasts as wet weight.

A 320 L of extract was obtained according to the method as shown in example 1. The extract was purified by employing active carbon column and ion exchange column according to the conventional method. To 4.5 L of purified concentrate was added an excessive amount of ethanol. A precipitate formed was collected on Buchner funnel and dried in vacuo to give 215 g of white powder. The white powder was high-purity UDP-N-acetylglucosamine disodium salt.

Results of purity test of the product obtained in examples are shown below.

HPLC analysis

A 300 mg of the product is precisely weighed and diluted with water to prepare diluent at a volume of 100 ml. A 10 μl of the diluent was analyzed. HPLC sorbent was HITACHI ANION GEL 3013N. The chromatogram of HPLC is shown in FIG. 1. In FIG. 1, the lower absorption peak is at 260 nm, and upper absorption peak is at 280 nm. Full scale of absorbance is 2.0, flow rate is 1 ml/min and chart speed is 0.5 cm/min. The sharp single peak in FIG. 1 demonstrate that the product of UDP-N-acetylglucosamine is high-purity with no other nucleotides.

Purity determined by UV absorption

The above-mentioned 3% solution of the product was diluted precisely 100-fold with 0.01N hydrochloric acid solution. Absorbance of the diluent at 262 nm was determined with HITACHI Spectrophotometer Type 100-30 at a light width of 1 cm. The measured value was 0.445. The concentration of stock solution was calculated according to the equation shown below employing molar absorption coefficient of uridine nucleotide (=9900):

[M]=A×100/9900

[M]×653=concentration of stock solution (%)

[M]: mole concentration;
A: absorbance
100: dilution ratio
653: molecular weight of UDP-N-acetylglucosamine disodium salt The concentration of the stock solution was calculated as 2.935%, which means that purity of the product (UDP-N-acetylglucosamine) is more than 97%.

Enzyme analysis

It was confirmed that the product of example 3 was high-purity UDP-N-acetylglucosamine by the reaction employing enzyme, UDP-N-acetylglucosamine pyrophospholyrase separated from bacteria belonging to Staphylococcus genus.

EXAMPLE 4

Production of UDP-N-acetylglucosamine by fermentation method employing sodium sulfate-added medium In this example, sodium sulfate was employed in place of sodium chloride as inorganic salt to increase osmotic pressure of a medium.

The procedure of example 1 was repeated except that 4% sodium sulfate was employed in place of 4% sodium chloride as shown in example 3 in seed medium and production medium to give 18.5 kg of yeasts as wet weight. The yeasts were extracted, purified and crystalized in the same way as example 3 to obtain 182 g of white powder. The white powder obtained was UDP-N-acetylglucosamine disodium salt having purity of more than 97% similar to the product of example 3.

Examples 5–8

Production by osmo-tolerant yeasts other than Zygosaccharomyces genus

The same method as example 1 was repeated except that each of *Pichia farinosa*, *Debaryomycos hansenii* and *Candida versatilis* was employed in place of *Zygosaccharomyces rouxii* as spawn and that sodium chloride concentration in a medium was 4%. All yeasts produced UDP-N-acetylglucosamine with lower yield than *Zygosaccharomyces rouxii*.

We claim:

1. A method for producing uridine diphosphate N-acetylglucosamine comprising the steps of:

(a) culturing yeast *Zygosaccharomyces rouxii* capable of growing in a medium having a salt concentration of at least 2%, provided that said yeast can also be grown in a medium having a salt concentration of less than 2%, in aerobic conditions in a medium having an inorganic salt concentration of about 2–8% while aerating said medium to maintain a dissolved oxygen concentration of 0.4 ppm or more; and (b) recovering uridine diphosphate N-acetylglucosamine from the cultured yeast.

2. The method according to claim 1, wherein said yeast is *Zygosaccharomyces rouxii* ATCC 52698.

3. The method according to claim 1, wherein, in step (a), said yeast is cultured while said medium is agitated.

4. The method according to claim 1, wherein, in step (a), the aeration is conducted so that the dissolved oxygen concentration of said medium remains in the range from 1 ppm to 7 ppm.

5. The method according to claim 1, wherein, in step (a), the aeration is conducted so that the dissolved oxygen concentration of said medium remains in the range from 2 ppm to 7 ppm.

* * * * *

UNITED STATES PATENT AND TRADEMARK OFFICE
CERTIFICATE OF CORRECTION

PATENT NO. : 5,674,715
DATED : October 7, 1997
INVENTOR(S) : Minoru Tomita, et al.

It is certified that error appears in the above-identified patent and that said Letters Patent is hereby corrected as shown below:

On the title page, item [54] and Column 1, lines 1-2 in the title , please delete "METHOD FOR PRODUCING URIDINE DIPHOSPHATE N-ACETYLGLUOSAMINE", and add --METHOD FOR PRODUCING URIDINE DIPHOSPHATE N-ACETYLGLUCOSAMINE--.

Signed and Sealed this

Twenty-second Day of September, 1998

Attest:

BRUCE LEHMAN

*Attesting Officer*            *Commissioner of Patents and Trademarks*